(12) United States Patent
Harbeck

(10) Patent No.: US 6,193,987 B1
(45) Date of Patent: Feb. 27, 2001

(54) LUBRICATING COMPOSITION FOR HANDS AND SKIN

(76) Inventor: Marie Helena Harbeck, 3202 Clumpgrass Cove, Austin, TX (US) 78735

( * ) Notice: Subject to any disclaimer, the term of this patent is extended or adjusted under 35 U.S.C. 154(b) by 0 days.

(21) Appl. No.: 09/248,573

(22) Filed: Feb. 11, 1999

(51) Int. Cl.[7] ............................. A61K 7/00; A61K 35/78; A61K 31/07
(52) U.S. Cl. ..................... 424/401; 424/195.1; 424/658; 514/725; 514/861; 514/863; 514/887; 514/937; 222/575
(58) Field of Search ................................. 424/401, 195.1, 424/658; 514/725, 861, 863, 887, 937; 222/575

(56) References Cited

U.S. PATENT DOCUMENTS

| 4,608,392 | * | 8/1986 | Jacquet et al. . | |
| 4,740,367 | | 4/1988 | Force et al. | 424/47 |
| 4,883,659 | * | 11/1989 | Goodman et al. . | |
| 5,244,679 | | 9/1993 | Freston | 424/659 |
| 5,431,911 | * | 7/1995 | Reynolds . | |
| 5,489,429 | | 2/1996 | Griat et al. | 424/401 |
| 5,683,704 | | 11/1997 | Ohba et al. | 424/401 |

* cited by examiner

Primary Examiner—Diana Dudash
Assistant Examiner—Alysia Berman
(74) Attorney, Agent, or Firm—Joseph F. Long

(57) ABSTRACT

A topical transdermal delivery system for lubricating and alleviating distressed skin conditions of the hands, and skin. It has as its constituents a mixture of organic safflower oil, flaxseed oil, tincture of benzoin, and organic beeswax blended in a cream-like base.

2 Claims, No Drawings

LUBRICATING COMPOSITION FOR HANDS AND SKIN

BACKGROUND-FIELD OF INVENTION

This invention relates to an organic skin lubricating composition with a potent alleviating affect on distressed hand and skin infirmities.

BACKGROUND-DESCRIPTION OF PRIOR ART

To the best of the applicant's knowledge the following is the most relevant prior art:

U.S. Pat. No. 4,740,367 Force, et al. 1988
U.S. Pat. No. 5,244,679 Freston. 1993
U.S. Pat. No. 5,489,429 Griat, et al. 1996
U.S. Pat. No. 5,683,704 Ohba, et al. 1997

The cosmetic industry is continually expanding its efforts in order to provide topical preparations which will moisten and soften the skin, eliminate chapping, chafing, redness and restore the skin to its natural condition, thus the combinations of skin-aggravating synthetic compositions employed continue to increase yearly.

Thus, synthetic surfactants, silicones, ammonia, alcohol's, solvents, acids, preservatives and the like are being incorporated into the compositions of the cited prior art to extend the shelf life of the cited compositions that are supplied to stores and supermarkets.

It will be appreciated that the expansion and growth of the cited prior art has devolved highly complex synthetic adjuvants for use in the formulations.

The problem with the use of the compositions of the cited prior art which make up the bulk of transdermal delivery systems are their chemical structures which are known to cause hand and skin irritations.

Alcohol, acids, solvents, synthetic preservatives, synthetic perfumes and colorants, and ammonia adjuvants incorporated into the compositions of the prior art cause dryness of the skin, rashes, allergies, atopic dermatitis, peeling, itching, cracking of the skin, and rashes.

Unfortunately, the cited prior art compositions have very relative effectiveness for distressed skin conditions, not allowing the treatment and alleviation of skin irritations related to allergic skin reactions to synthetic adjuvants, so there is a need in the art for organic compounds that can be used as potent actives for topical treatments for skin.

The said prior art compositions do not employ the massive quantities of organic vegetable oil and organic beeswax compositions that this invention incorporates.

In terms of effectiveness, the said cited prior art compositions provide unsatisfactory skin penetration and supplying properties that do not leave the hands and skin satiny smooth for up to 12 hours.

The said cited prior art compositions do not provide organic safflower oil or flaxseed oil, in their formulas to restore essential oil lipids that are essential to nourish healthy skin.

Accordingly, the said prior cited art compositions do not include the high volume of organic essential oils to perfume their compositions due to the prohibitively expensive manufacturing costs.

OBJECTS AND ADVANTAGES

Accordingly, besides the objectives and advantages of the topical application for alleviation of distressed skin described in the above patent, several objectives and advantages of the present invention are:

a) to provide an alcohol free topical skin preparation.
b) to provide an essential oil as an organic antiseptic adjuvant to fight environmental aggressors of the skin.
c) to provide a topical skin preparation that has potent effectiveness in the treatment of skin infirmities, such as atopic dermatitis, atopic eczema, chapping, rough skin, dryness, itching, skin allergies related to synthetic substances and the like.
d) to provide a high volume of organic skin vegetable oil compositions for swift transdermal delivery.
e) to provide satisfactory skin penetration of the said composition and supplying properties that leave the hands and skin satiny smooth for up to twelve hours.
f) to provide a high volume of organic essential oils to perfume the said composition for the users pleasure.
g) to provide a high volume of organic safflower oil, and flaxseed oil in the said composition to feed lost lipids to the dermis.
h) to provide an urgent need that exists for an emollient like the present invention to the dermatological field.
i) which will alleviate the symptoms of atopic dermatitis, rough skin, dryness, cracking, atopic eczema, chapping, itching and allergic skin reactions due to ammonia, solvents, acids, steroid, alcohol substances, and synthetic perfume, preservatives, and colorant substances.
j) which will provide an organic beeswax substance that bonds lubricating, hydrating, moisturizing and antiseptic adjuvants to the skin up to twelve hours.
k) which will provide an organic calming and moisturizing composition to the skin after micro-derma skin peels.

Thus, an urgent need exists for an application like the present invention, that employs a high volume of organic flaxseed and safflower oils plus organic liquid vitamins to feed the skin with nutritive organic vegetable oil lipids without the addition of synthetic adjuvants to achieve its purposes. Further advantages of this invention are the employment of an organic wax substance and an organic antiseptic substance that bonds to the skin to fight environmental skin aggressors, protecting and leaving the hands and skin moisturized and satiny smooth for up to twelve hours. Still further objects and advantages will become apparent from a consideration of the ensuing descriptions.

SUMMARY OF THE INVENTION

A potent non-sticky, organic, preservative free topical composition for treating, alleviating and protecting distressed hand and dry skin conditions, including atopic dermatitis, rough skin, dryness, atopic eczema, cracking, itching and allergic skin reactions to alcohol, synthetic substances, is provided for swift transdermal delivery, which includes flaxseed oil, safflower oil, tincture of benzoin, organic beeswax, liquid vitamin A, and oil of lavender blended together in a cream base.

DESCRIPTION OF THE INVENTION

The present invention includes the surprising discovery that organic safflower and flaxseed oils can be used as active principals in topical applications to treat distressed skin conditions attributed to ichthyosis, atopic eczema, and atopic dermatitis.

In accordance with the present invention there is provided a number of formulations where safflower oil, and flaxseed oil, can be employed with organic beeswax to aid in the safe care of distressed human skin conditions. The embodiment of the invention follow to illustrate the formulations.

EXAMPLE NO. 1

Hand and Skin Cream
Ingredients:
6 tablespoons purified water
1 tablespoon organic white beeswax
1 tablespoon emulsifying wax cetearyl alcohol & polysorbate 60 called LipowaxP, purchased from Lipo Chemicals Inc, 207 19th Avenue, Paterson, N.J. 07504.
2 teaspoons safflower oil
2 teaspoons sweet almond oil
2 teaspoons apricot kernel oil
2 teaspoons vitamin E oil
2 teaspoons liquid vitamin A
1½ teaspoons cocoa butter
1 teaspoons flaxseed oil
1 teaspoon jojoba oil
1 teaspoon essential lavender oil
1 teaspoon glycerin
1 teaspoon liquid paraffin
1 teaspoon stearic acid
¼ teaspoon powdered borax
6 drops tincture of benzoin
Formulation Process:
place safflower oil, sweet almond oil, apricot oil, vitamin E oil, jojoba oil, flaxseed oil, vitamin A oil, emulsifying wax, beeswax, stearic acid, liquid paraffin, cocoa butter and glycerin in a container over hot water to form a mixture:
   stirring said mixture over hot water until dissolved;
   simultaneously placing purified water, powdered borax, and tincture of benzoin, in another container over hot water to form a mixture:
     stirring said mixture over hot water until dissolved;
     removing said mixtures from heat and blending both mixtures until said mixtures cool and turn white;
     adding essential oil of lavender to mixture; and
     blending mixture until it thickens;
      whereby the ingredients are formed into a soft fragrant cream-like base.

Massage Lotioii
Ingredients:
6 teaspoons flaxseed oil
4 teaspoons safflower oil
2 teaspoons sweet almond oil
2 teaspoons apricot kernel oil
2 teaspoons vitamin E oil
2 teaspoons liquid vitamin A
1½ teaspoons cocoa butter
1 teaspoon jojoba oil
1 teaspoon essential lavender oil
1 teaspoon glycerin
1 teaspoon liquid paraffin
6 drops tincture of benzoin
Formulation Process:
Place safflower oil, sweet almond oil, apricot kernel oil, vitamin E oil, vitamin A oil, cocoa butter, flaxseed oil, jojoba oil, glycerin, liquid paraffin, into a container to form a mixture:
   stirring said mixture until blended;
   adding essential lavender oil, and tincture of benzoin to mixture; and
   blending mixture; wherein the ingredients are formed into a soft fragrant lotion.

EXAMPLE NO. 3

Hand Lotion
Ingredients:
10 tablespoons purified water
1½ tablespoons natural white beeswax
1 ½ tablespoons emulsifying wax
4 teaspoons flaxseed oil
4 teaspoons safflower oil
2 teaspoons sweet almond oil
2 teaspoons apricot kernel oil
2 teaspoons vitamin E oil
4 teaspoons liquid vitamin A
3 teaspoons cocoa butter
2 teaspoons jojoba oil
2 teaspoons liquid paraffin
1 teaspoon essential oil of rosemary
1 teaspoon essential oil of peppermint
1 teaspoon essential oil of orange
1 teaspoon glycerin
1 teaspoon stearic acid
1 teaspoon powdered borax
6 drops tincture of benzoin
Formulation Process:
Place safflower oil, sweet almond oil, apricot kernel oil, vitamin E oil, vitamin A oil, cocoa butter, flaxseed oil, jojoba oil, glycerin, liquid paraffin, stearic acid, natural white beeswax, wax, in a container over hot water to form a mixture:
   stirring said mixture over hot water until dissolved;
   simultaneously placing purified water, powdered borax, in another container over hot water;
   stirring said mixture over hot water until borax dissolves;
   removing said mixtures from heat and blending both mixtures until said mixtures cool and turn white;
   adding essential oils, and tincture of benzoin to mixture; and
   blending mixture until it thickens; wherein the ingredients are formed into a soft fragrant cream.

EXAMPLE NO. 4

Foot Cream
Ingredients:
4 tablespoons purified water
1 tablespoon natural white beeswax
1 tablespoon wax
4 teaspoons vitamin E oil
4 teaspoons safflower oil
2 teaspoons sweet almond oil
2 teaspoons apricot kernel oil
4 teaspoons liquid vitamin A
2 teaspoons cocoa butter
3 teaspoons flaxseed oil
1 teaspoon jojoba oil
2 teaspoons essential lavender oil
1 teaspoon glycerin
1 teaspoon stearic acid
¼ teaspoon powdered borax
10 drops tincture of benzoin
Formulation Process:
Place safflower oil, sweet almond oil, apricot kernel oil, vitamin E oil, vitamin A oil, cocoa butter, flaxseed oil, jojoba oil, glycerin, stearic acid, natural white beeswax, wax, in a container over hot water to form a mixture:
   stirring said mixture over hot water until dissolved;
   simultaneously placing purified water, powdered borax, in another container over hot water;

stirring removing said mixtures from heat and blending both mixtures until said mixtures cool and turn white;

adding essential lavender oil, and tincture of benzoin to mixture; and blending mixture until it thickens; wherein the ingredients are formed into a soft fragrant cream said mixture over hot water until borax dissolves

THEORY OF INVENTION

While I believe that the lubricating, healing, protective and softening properties of safflower and flaxseed oil lipids, liquid vitamins and tincture of benzoin, emulsified in organic beeswax are essential for the repair of distressed and damaged skin, I don't wish to be bound by this."

OPERATION OF THE INVENTION

As noted, the composition hereof comprises a new and potent topical application which is applied to the dermal areas of the hands and skin to alleviate distressed skin conditions.

This invention is highly effective in the treatment and alleviation of distressed skin related to allergic skin reactions to the adjuvants in the cited prior art compositions, plus this invention incorporates massive quantities of organic skin feeding and lubricating compositions.

In terms of effectiveness, this invention provides swift transdermal delivery, and superior and potent skin penetration and supplying properties that leave the skin satiny smooth for up to twelve hours.

For a more complete understanding of the present invention reference is made to the following examples. The following examples are illustrative of the present inventions efficacy and are not intended in any way as a limitation upon the scope thereof.

EXAMPLE 1

The composition of the present application was applied thrice daily to the hands of a woman suffering from severe atopic dermatitis. Her hands and fingers were severely affected, with weeping and bleeding from the cracks in her skin. Within four days after applying, the composition, the cracks almost healed and most of the damaged skin had healed. Within ten days, the cracks were completely healed and a layer of new skin had appeared. The skin displayed no signs of atopic dermatitis. After two months of use, the thick damaged skin was replaced with new pink skin.

EXAMPLE 2

The composition of the present application was applied twice daily to the face of an adolescent boy suffering from a red, dry, scaly, itchy rash on his nose. Within four days, the itch, redness and rash had disappeared, and the skin was healed. After one month of use, the rash and itchiness have not reappeared.

EXAMPLE 3 a) Male user found present application superior for alleviating and preventing facial rashes due to shaving.

b) Within seven days of use of present application, said male user found that a scaly, brown pigmented area on his forehead disappeared.

EXAMPLE 4

After two months of consistent daily use of present application, a 78 year old diabetic woman found that the cracked, dry skin condition on her amputated limb, was alleviated, and continued use of present application prevented these conditions from occurring.

EXAMPLE 5

To evidence the efficacy of the present application, a series of individuals suffering from various degrees of dermatological infirmities were treated with the composition of the present application in the offices of a plastic surgeon. Compared to composition hereof to commercially available products, some of which contain one or more of the components hereof The results based upon the efficacy of the present invention are set forth hereinafter.

a) within one week of use, present invention healed cracks on heels from dry skin condition.

b) present invention alleviated dry hand and skin conditions within 3 days after using invention.

c) users found present invention superior for moisturizing and calming hands, throat and facial skin after a microderma peel.

d) an offer has been made to sell present invention through the offices of the above-mentioned plastic surgeon.

e) from the above-mentioned examples, an offer has been tended to the inventor for the license to manufacture and distribute to the public the present invention.

CONCLUSION, RAMIFICATION, AND SCOPE OF INVENTION

Thus, from the preceding it will be readily perceived by the reader that an urgent need exists for this topical application for alleviation of distressed hand and skin conditions denoted heretofore, but which, also, can be used to prevent such conditions from occurring.

It provides a new, safe, superior, highly effective, reliable cream.

It leaves hands and skin satiny smooth for up to twelve hours.

It can be used by humans and animals suffering from various degrees of dematological infirmities.

It provides an alcohol, solvent and acid free topical skin preparation.

It provides an antiseptic organic essential oil to fight environmental aggressors.

It provides potent effectiveness in the treatment and management of atopic dermatitis, atopic eczema, chapping, rough skin, dryness, itching, skin allergies related to synthetic substances and the like.

It restores a high volume of organic oil lipids essential to healthy skin

It provides an urgent commercial need that exists in the dermatological field.

It provides an organic beeswax substance that bonds lubricating, hydrating, and moisturising adjuvants to the skin.

It provides a calming and moisturing composition to the skin after microderma peels.

It provides a high volume of essential oils to perfume the composition for the users pleasures While the above description contains many specificities, these should not be construed as limitations on the scope of the invention, but merely providing illustrations of some of the presently preffered embodiments of this invention.

Many other variations are possible. For example, it is additionally possible to add to the present invention many other adjuvants such as avocado oil, sesame oil, emu oil, allantoin (anti-inflammatory agent), vitamins, antibiotics, organic ultraviolet filters, color pigments, floral waters, and various additional essential oils such as gardenia, rose, orange, rosemary, and peppermint.

Accordingly, the scope of the invention should be determined not by embodiments illustrated, but by the appended claims and their legal equivalents.

I claim:

1. A topical composition for alleviation and treatment of dermal infirmities of the hands and skin which comprises a composition of approximately:

- from 2 teaspoons to 4 teaspoons safflower oil,
- from 1 teaspoon to 6 teaspoons flaxseed oil,
- from 1 tablespoon to 1½ tablespoons white beeswax,
- from 2 teaspoons to 4 teaspoons vitamin A,
- from 6 drops to 10 drops tincture of benzoin,
- from 1 teaspoon to 2 teaspoons lavender oil,
- from 4 tablespoons to 12 tablespoons purified water,
- from 1 tablespoon to 1½ tablespoons emulsifying wax,
- 1 teaspoon stearic acid,
- from 1 teaspoon to 2 teaspoons liquid paraffin,
- ¼ teaspoon powdered borax,
- 2 teaspoons sweet almond oil,
- 2 teaspoons apricot kernel oil,
- from 2 teaspoons to 4 teaspoons vitamin E oil,
- from 1 teaspoon to 2 teaspoons jojoba oil,
- from 1½ teaspoons to 2 teaspoons cocoa butter,
- and 1 teaspoon glycerin, whereby a topical composition is provided for alleviating and treating the symptoms of dry hand and skin conditions.

2. A process for making a composition for alleviation and treatment of dermal infirmities of the hands and skin, comprising the steps of:

placing safflower oil, sweet almond oil, apricot oil, vitamin E oil, jojoba oil, flaxseed oil, vitamin A oil, emulsifying wax, white beeswax, stearic acid, liquid paraffin, cocoa butter and glycerin in a container over hot water to form a mixture, stirring said mixture over hot water until dissolved, simultaneously placing purified water, powdered borax and tincture of benzoin, in another container over hot water to form a mixture:

stirring said mixture over hot water until dissolved:

removing said mixtures from heat and blending both mixtures until said mixtures cool and turn white:

adding essential oil of lavender to mixture, and blending mixture until it thickens, whereby the ingredients are formed into a soft fragrant—cream—base.

* * * * *